United States Patent
Chen (12)

(10) Patent No.: US 6,168,912 B1
(45) Date of Patent: *Jan. 2, 2001

(54) METHOD AND KIT FOR MAKING A MULTIDIMENSIONAL COMBINATORIAL CHEMICAL LIBRARY

(75) Inventor: Hao Chen, Adelphia, MD (US)

(73) Assignee: Martek Biosciences Corporation, Columbia, MD (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/590,279

(22) Filed: Jan. 23, 1996

(51) Int. Cl.$^7$ .............................. C12Q 1/00; G01N 33/53; G01N 33/566; G01N 33/536
(52) U.S. Cl. ................................. 435/4; 435/7.1; 435/7.2; 435/DIG. 50; 436/501; 436/518; 436/536
(58) Field of Search .................................... 436/536, 501; 436/518; 435/7.1, 7.2, 4

(56) References Cited

U.S. PATENT DOCUMENTS

| 5,306,718 | 4/1994 | Lauffer et al. . |
|---|---|---|
| 5,393,669 | 2/1995 | Brown . |
| 5,565,324 | * 10/1996 | Still et al. . |

OTHER PUBLICATIONS

Meyers, et al., "Multiple Simultaneous Synthesis of Phenolic Libraries", *Molecular Diversity* 1:13–20 (1995).
DeWitt et al., "'Diversomers': An Approach to Nonpeptide, Nonoligomeric Chemical Diversity", *Proc. Natl. Acad. Sci., USA* 90:6909–6913 (1993).
Pavia et al., "The Generation of Molecular Diversity", *Bioorganic & Molecular Chemistry Letters* 3(3):387–396 (1993).
Sanders et al., "Cholinergic Agents: Aldehyde, Ketone, and Oxime Analogues of the Muscarinic Agonist UH5", *Bioorganic & Medicinal Chemistry Letters* 2(8):803–808 (1992).
Moos et al., "Chapter 33. Recent Advances in the Generation of Molecular Diversity", *Annual Reports in Medicinal Chemistry* 28:315 (1993).
Pavia et al., "Chapter 3. Cognition Enhancers", *Annual Reports in Medicinal Chemistry* 25:21–29 (1989).
Pavia et al., "Structure–Activity Studies on Benzhydrol–Containing Nipecotic Acid and Guvacine Derivatives as Potent, Orally–Active Inhibitors of GABA Uptake", *J. Med. Chem.* 35:4238–4248 (1992).
R.W. Horton, "Behavioral effects of allylglycine (2–amino–4–pentenoic acid) and 2–keto–4–pentenoic acid following focal injection into the rat cerebellum and caudate nucleus", Jun., 1978, British Journal of Pharmacolgy, vol. 63, Issue 2, pp. 381P.
S.K. Fisher, et al., "Some properties of Guinea Pig Brain Glutamate Decarboxylase and its Inhibition of the Convulsant Allylglycine (2–amino–4–Pentenoic Acid)" Aug., 1974, Journal of Neurochemistry, vol. 23, No. 2, pp. 427–433.
G. Rodriguez, et al., "2–Amine 4–Pentenoic Acid (Allylglycine): A Proposed Tool For the Study of GABA Mediated Systems" Int. Journal of Neurosci., Sep. 1971, vol. 2, Issue 3, pp. 137–144.
Janda, K. D. "Tagged versus Untagged Libraries . . . " Proc. Natl. Acad. Sci. USA, vol. 91, pp. 10779–10785, Nov. 1994.*
Sinha et al. *Tetrahedrm Letters* 36(51) 9257–9260 (1995).*
Bolton et al. *Tetrahedrm Letters* 53(19) 6611–6634 (1997).*
Shimizu et al. *Syn Lett* (1996) pp. 1112–1114.*
Martin et al., J. Med. Chem. (1992) vol. 35 pp. 1710–1721.*
Schildknecht, "Kirk–Othmer Encyclopedia of Chemical technology" Wiley Interscience, John Wiley & Sons, Inc. USA pp. 109–129 1978.*
Streitwieser et al. "Introduction to Organic Chemistry" MacMillan Publishing Co., Inc., USA pp. 579–580 1981.*
Richey "Fundamentals of Organic Chemistry" Prentice Hall, Inc., NJ, USA pp. 51–67. 1983.*
Gordon et al., J. Med. Chem. (1994) vol. 37(10) pp. 1385–1401.*

* cited by examiner

*Primary Examiner*—Jyothsna Venkat
*Assistant Examiner*—Maurie E. Garcia
(74) *Attorney, Agent, or Firm*—Brobeck Phleger & Harrison, LLP

(57) ABSTRACT

Building blocks for making a combinatorial chemical library comprise α-allyl carboxylic acids and their functionalized derivatives. These are covalently linked by monotonous or diverse linkages. These can be conformationally constrained by cyclization and annelation. Kits comprising diverse α-allyl carboxylic acids can be used to make libraries.

5 Claims, 12 Drawing Sheets a) ArCHO/TSA/4Å molecular sieves/refluxing Toluene; b) i, LDA/THF (−78°C), ii Allylbromide/HMPA; iii, CH₃OH/H₂O/TFA a.) p-methoxybenzylchoride/NaH/DMF; b.) LDA/THF (-78°C); ii, allylbromide/HMPA; c.) CH₃OH/NaOH(aq. 1N)

(5)

(6)

(7)

(8)

(9)

(10)

(11)

(12)

(13)

METHOD AND KIT FOR MAKING A MULTIDIMENSIONAL COMBINATORIAL CHEMICAL LIBRARY

TECHNICAL FIELD OF THE INVENTION

The invention relates to the field of drug research. In particular, it relates to new methods for generating chemical libraries using combinatorial methods, for development and screening of new drugs.

BACKGROUND OF THE INVENTION

Conventional drug discovery involves mailing thousands of compounds and testing them for biological activities to find a "lead" compound. The success rate of finding a drug is <1/10,000 compounds tested. The time required is about seven to ten years. The cost is in the millions of dollars.

Recent developments in drug discovery via the combinatorial approach have had an impact on the pharmaceutical industry. (See Bibliography.) The cost of finding a drug may be lowered because the new approach is capable of supplying compounds readily and cheaply. Some compounds developed using this approach are oligomeric molecules (peptides, nucleotides, oligosaccharides) and others are non-oligomeric molecules ("small molecules", i.e., less than ~m.w. 600). The size of a linear oligomeric library depends on the number of monomeric units and the length of the oligomers assembled. For instance, using a two substrate matrix (A and B) there are four possible compounds (AA, AB, BA, and BB) in the library of dimers. Non-linear libraries are made by simultaneously transforming a large group of chemical substrates under a given set of conditions to afford a group of compounds that are different from the starting materials. The latter type of library may not greatly expand the number of compounds, nevertheless, this operation leads to the formation of a new collection of compounds efficiently.

Combinatorial chemistry was born of the marriage between mass screening and medicinal chemistry. It was developed in response to the statistical evidence that drug discovery is a "numbers game". Classical mass screening involves testing tens of thousands of compounds and natural extracts looking for a lead compound with a desired biological activity. Classical medicinal chemistry, based on the lead compound identified, modifies the lead compound, atom by atom, group by group making structural analogues, with the goal of improving activity that may advance the lead compound to a clinically useful drug. Combinatorial chemistry combines the two classical approaches. By allowing a given set of starting materials to react with each other under a given set of conditions, the combinatorial approach generates a large number of compounds that are defined by the combinatorial probability. If enough compounds are made, one of them will be a lead compound or may even be a clinically useful drug. Furthermore, this approach can make structural analogues simultaneously. A stringent screening process can select the best drug candidate among structural analogues. The combinatorial approach combines lengthy initial mass screenings and medicinal chemical optimizations into a single process. Thus this approach is favorable with respect to both efficiency and speed.

However, problems have arisen in using both linear oligomeric libraries and small molecule libraries for drug discovery. First, the number of compounds generated by the conventional combinatorial libraries is relatively small. For instance, with 20 common amino acids, a hexapeptide (linear oligomeric) library contains only 64 million compounds. For small molecule libraries, the number of compounds generated is even smaller. Second, the compounds present in conventional combinatorial libraries lack chemical diverstiy. For the linear oligomeric library, a major contributor to the lack of diversity is the monotonous chemical linkages; for small molecule libraries, the lack of diversity is caused by the limited chemical transformations possible with the chemical substrates used.

Thus there is a need in the art for additional methods of generating large numbers of diverse chemicals for testing for biological activities.

SUMMARY OF THE INVENTION

It is an object of the invention to provide a method of making "building blocks" and using them to build a combinatorial library.

It is an object of the invention to provide a method of making a chemical library.

It is another object of the invention to provide a kit for creating a combinatorial chemical library.

It is another object of the invention to provide combinatorial chemical libraries.

These and other objects of the invention are provided by one or more of the embodiments described below. In one embodiment of the invention a method is provided of making a chemical library. The method comprises the step of:

converting in parallel a set of at least two carboxylates having a structure $R^1R^2CHCOR^3$ to α-allyl carboxylate monomers having a structure

wherein $R^{1-2}$ are independently H, alkyl, aryl, carbocyclic, heterocyclic, or chemical moieties containing heteroatoms O, N, S, X, or P;

$COR^3$ is an amide, an ester, or a carboxyl group; and $R^{4-8}$ are independently H, aryl, or alkyl.

In another embodiment of the invention a method of making a chemical library is provided. The method comprises the step of:

converting in parallel a set of at least two α-allyl carboxylate monomers to form monomer derivatives, said monomers having a structure

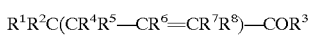

wherein $R^{1-2}$ are independently H, alkyl, aryl, carbocyclic, heterocyclic, or chemical moieties containing heteroatoms O, N, S, X, or P, wherein X is a halogen;

$COR^3$ is an amide, an ester, or a carboxyl group; and $R^{4-8}$ are independently H, aryl, or alkyl; and wherein said step of converting comprises converting any of $R^4$–$R^8$ of said monomers to other chemical moieties.

In another embodiment of the invention a kit for creating a combinatorial chemical library is provided. The kit comprises:

a set of monomers consisting of at least two α-allyl carboxylic acids, said acids having a structure

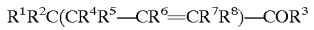

wherein $R^{1-2}$ are independently H, alkyl, aryl, carbocyclic, heterocyclic, or chemical moieties containing heteroatoms O, N, S, X, or P;

COR$^3$ is an amide, an ester, or a carboxyl group; and

R$^{4-8}$ are independently H, aryl, or alkyl;

and wherein said monomers are in separate compartments of said kit.

According to yet another embodiment of the invention another method is provided for making a combinatorial library. The method comprises the steps of:

converting in parallel a set of at least two α-allyl carboxylate monomers to form monomer derivatives, the monomers having a structure

wherein R$^{1-2}$ are independently H, alkyl, aryl, carbocyclic, heterocyclic, or chemical moieties containing heteroatoms O, N, S, X, or P;

COR$^3$ is an amide, an ester, or a carboxyl group; and

R$^{4-8}$ are independently H, aryl, or alkyl;

wherein the step of converting comprises converting any of R$^4$–R$^8$ of the monomers to other chemical moieties;

covalently linking at least two monomers to form oligomers, wherein the monomers are selected from the group consisting of: the α-allyl carboxylate monomers and the monomer derivatives; and testing the oligomers for a biological activity.

In still another embodiment of the invention combinatorial libraries are provided. Such libraries are made by the processes described here. Members of the libraries which demonstrate biological activities are identified and provided.

Thus the present invention provides the art with the tools and methods for creating diverse chemical libraries which themselves have great chemical diversity. This is a great boon to the art of drug screening and development.

DETAILED DESCRIPTION OF THE PREFERRED EMBODIMENTS

Figure 1:
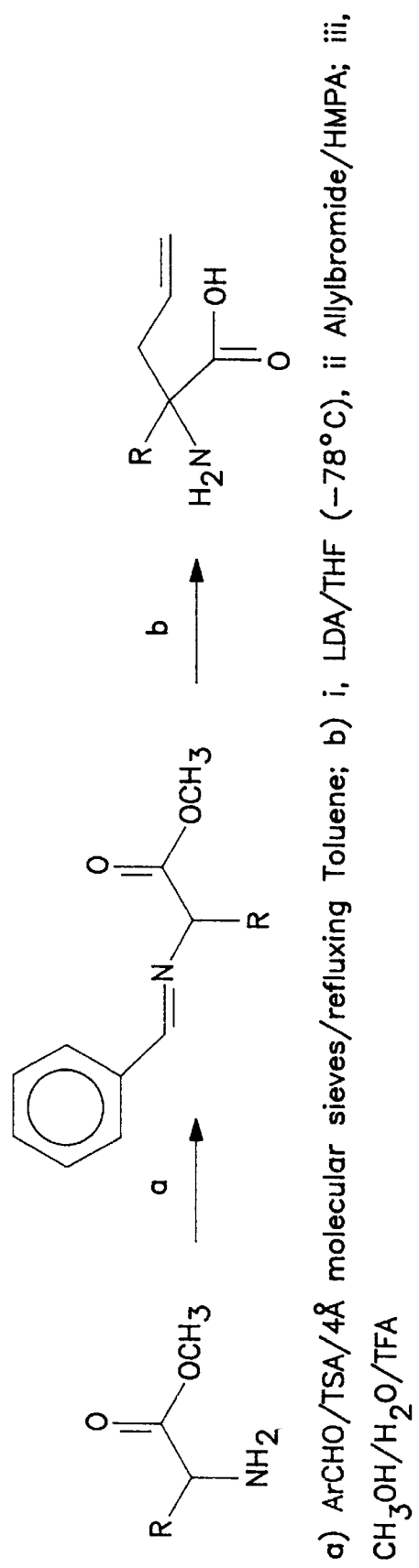
FIG. 1 shows direct alkylation of an amino acid methyl ester hydrogen chloride.

It is a discovery of the present invention that α-allyl carboxylic acids make ideal starting materials for the generation of diverse chemical libraries. These acids, termed "monomers" herein, are readily synthesized using readily available acids and allyl halides and their corresponding alcohols. The monomers themselves can be very diverse, due to the large number of available organic acids, with diverse side chains and backbones.

The α-allyl carboxylic acids of the present invention have the structure

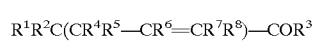

wherein R$^{1-2}$ are independently H, alkyl, aryl, carbocyclic, heterocyclic, or chemical moieties containing heteroatoms O, N, S, X (halogen), or P;

COR$^3$ is an amide, an ester, or a carboxyl group; and

R$^{4-8}$ are independently H, aryl, or alkyl. The α-allyl carboxyl compounds and their derivatives are useful as building blocks for the construction of multidimensional combinatorial libraries.

α-Allyl carboxylate monomers can be made by the alkylation of carboxylates, such as esters and amides, represented by a general formula of R$^1$R$^2$—CH—COR$^3$. When the esters or amides are converted to the α-allyl carboxyl compounds, the α-proton (H) is replaced with an allylic functionality, i.e. —CR$^4$R$^5$—CR$^6$═CR$^7$R$^8$, for example from an allyl halide or corresponding alcohol.

The distinction of the combinatorial approach of the subject invention is that the total combinatorial possibilities are controlled and generated by a multitude of factors and variables, i.e., it is multidimensional. These factors and variables are: (1) the number of chemical substrates, (2) the number and the type of chemical reactions (that transform the allylic functionality), (3) the number and (4) the type of chemical reactions that are used for the joining of monomers, (5) the order of different reactions introduced in the process, and (6) the stereochemical selectivity and outcome of the chemical and assemblies. This combinatorial approach generates more chemically diverse organic compounds than are made by conventional methods of making combinatorial libraries.

The theoretical number of molecular possibilities using multidimensional combinatorial libraries is far greater than using standard combinatorial libraries. For example, consider use of only two starting units (two amino acids, for example) converted into their respective α-allylic carboxylic acid forms (a=2). Assuming that each of the two α-allylic carboxylic acids can be converted into 4 different molecules through their allylic functionality (b=4), then:

a 1-Dimensional combinatorial library would have (a·b) or (2·4=8) members. Assuming a combinatorial library of trimers (x=3), then:

a 2-Dimensional combinatorial library would have (a·b)$^x$ or (8$^3$=512) members.

Assuming that each of the eight different functionalized monomers can be linked through any of 3 possible functional groups (y=3), then:

a 3-Dimensional combinatorial library would have (a·b)$^{x \cdot y}$ or (8$^9$=134 million) members.

If each of the linkages has 2 possible stereoisomers (z=2), then:

a 4-Dimensional combinatorial library would have (a·b)$^{x \cdot y \cdot z}$ or (8$^{18}$=18×10$^{15}$) members.

Whereas a standard trimer combinatorial peptide library of two amino acids would only have (2)$^3$ or 8 theoretical members, a 4-dimensional combinatorial library using the above approach and starting with the same two amino acids would lead to $36 \times 10^{15}$ theoretical members.

Likewise a 4-dimensional combinatorial library of dimers (x=2) starting with the α-allylic derivatives of 20 amino acids (a=20) would yield a theoretical library of $(20 \cdot 4)^{2 \cdot 3 \cdot 2} = 80^{12}$ or about $10^{18}$ dimers, whereas the standard peptide library would only yield $(20)^2$ or 400 possible dipeptides. Dimers of amino acids have a particular advantage of being low molecular weight (less than 500), drug-like molecules.

It is desirable that large numbers of starting reactants be used to increase the ultimate diversity. At least two carboxylates or monomers are desirable, although use of more is favored. Typically at least three, four, or five carboxylates or monomers are used. Reactions are typically carried out in parallel, which may mean simultaneous reactions in separate vessels, or quasi-simultaneous reactions. Quasi-simultaneous reactions are reactions done as part of a single project, however, they may be done on separate days, weeks, or even months, so long as they are eventually used in a single enterprise. A single enterprise, for example, is the covalent linking of monomers to form oligomers, or the screening of a set of monomers or oligomers in a particular biological assay.

1. Preparation of the α-allylic Starting Materials

Introduction of an allylic functionality to the α-position of carboxylic acids makes available a large collection of branched-chain unsaturated carboxylic acids. With the newly introduced functionality, these carboxylic acids may be used to construct chemical libraries. The allylic group can be introduced to the α-position of the acids in a variety of different ways. Examples described herein use amino acids as the carboxylic acids for demonstration purposes only. The invention is not, however, limited to the use of amino acids as the carboxylate starting materials.

A. Introduction of Allylic Functionality by Direct Alkylation

The first example of direct alkylation, shown in FIG. 1, gives an unprotected α-allyl amino acid. Amino acid esters are used as starting materials. By treating the amino acid with benzaldehyde, trace amounts of acid, and in the presence of a dehydrating agent (e.g., 4 Å molecular sieves, or $Na_2SO_4$), benzylideneamino acid esters are formed. The acidic proton attached to the α-position of the carboxyl is extracted with base, for example, lithium diisopropylamide or NaH, and the α-position is alkylated with an allylhalide. The ester and the benzylidene are removed under acidic conditions to give a free α-allyl carboxylic acid.

Figure 2:
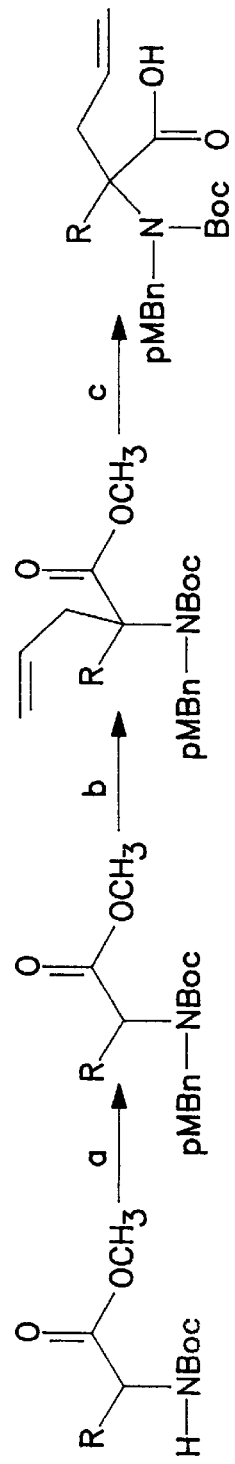
FIG. 2 shows direct alkylation of a protected amino acid.

The following example starts with protected amino acids and yields a protected α-allyl amino acid. As shown in the FIG. 2, two acidic protons (the carboxylic and amide protons) were sequentially removed and displaced by formation of an ester, followed by introduction of the N-p-methoxybenzyl group. The acidic proton attached to the α-position of the carboxyl functionality is extracted with lithium diisopropylamide at −78° C. The α-carbanion displaces bromide when the allylbromide is added to give an α-allyl ester, which is hydrolyzed under basic conditions to its corresponding acid, if desired.

These reaction sequences (FIGS. 1 and 2) give a high product yield. Moreover, the sequence in FIG. 1 gives an α-allyl amino acid without extensive functionality protections.

B. Introduction of Allylic Functionality by Enolate Rearrangements

Figure 3:
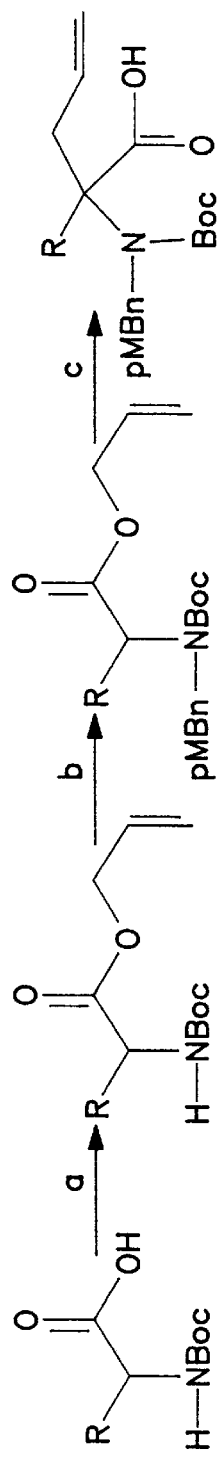
FIG. 3 shows a reaction scheme for making α-allyl carboxylic acids using an Ireland-enolate Claisen rearrangement.

The allylic functionality can be introduced via rearrangement of an acid enolate allyl ester, using an Ireland-enolate Claisen rearrangement. As shown in FIG. 3, the protected (t-Boc) amino acid is first converted to the allyl ester by treating the acid with allylbromide under basic conditions. The amide proton is then removed by the hydride and replaced with a p-methoxybenzyl group. The ester enolate is made by extracting the α-proton with lithium diisopropylamine, and the enolate is trapped with the trimethylsilyl groups. At elevated temperature, such as that of refluxing THF, the acid enolate rearranges itself to give the α-allyl carboxylic acid.

The advantage of using such a reaction sequence for the introduction of an allylic functionality is the ease in recovering the product, α-allyl carboxylic acid, in pure form. Due to differences between the starting material, an ester, and the end product, an aqueous soluble (under basic conditions) organic acid, the α-allyl carboxylate may be harvested in excellent chemical purity via simple liquid-liquid extraction. No further chemical purification is necessary and racemic product can be used directly for further chemical transformations as desired, or separated into the component racemates by methods well known in the art.

2. Preparation of the Allylic Derivatives

The branched-chain unsaturated carboxylic acids made by the introduction of an allylic group can be used to construct non-oligomeric small molecule-libraries via multiple simultaneous or parallel chemical transformations. The introduction of an allylic functionality, for example, into a carboxylic acid, such as the amino acids, introduces a reactive 3-carbon-unit to the native compound. This three-carbon-unit may undergo two types of chemical transformations. One is related to the double bond, i.e., the olefin; the other is associated with the allylic. The following discussion and reaction schemes depict a few examples in which the olefin and allylic systems may undergo a variety of transformations. Some oxidative examples in the later section demonstrate the utility of these α-allyl carboxylic acids.

Figure 4:
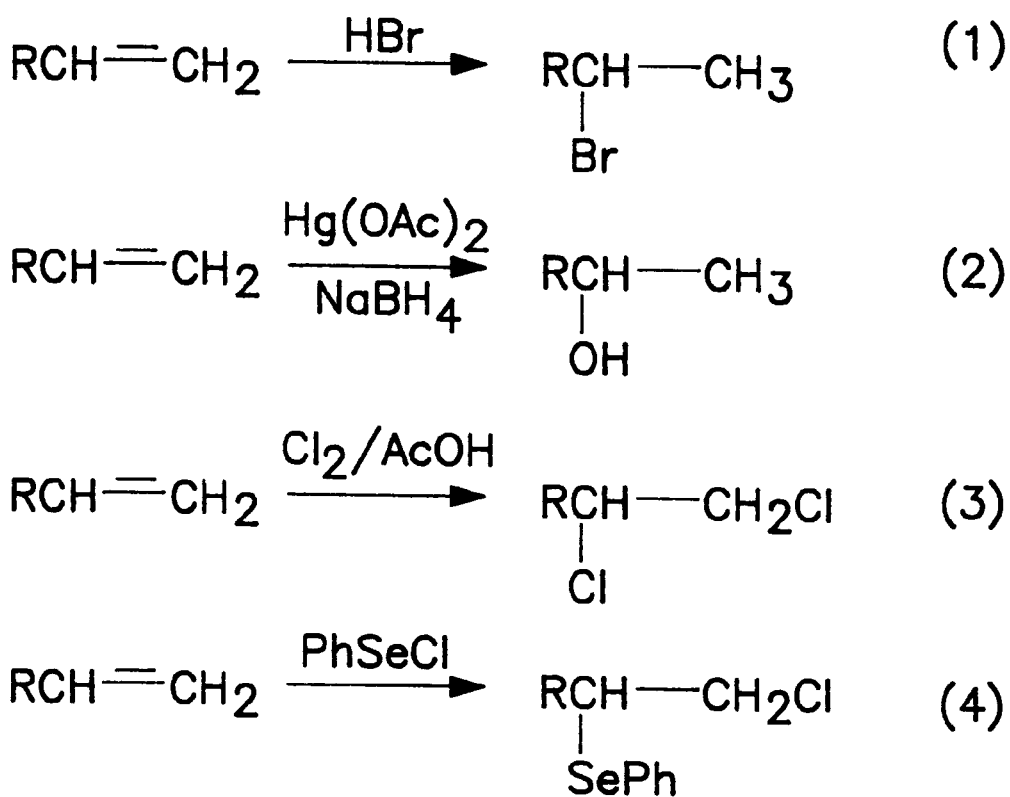
FIG. 4 shows electrophilic addition across the carbon-carbon double bond.

A. Chemical Transformations Based on the Carbon—Carbon Double Bond i. Electrophilic Additions to Carbon—Carbon Double Bonds The most general reaction involving the carbon—carbon double bond is the addition of electrophilic reagents. A few examples of electrophilic addition are listed in FIG. 4. As shown in the FIG. 4, the addition of hydrogen bromide to the olefin gives a brominated compound (1); the addition of mercuriacetate followed with a borohydride treatment adds a water molecule across the double bond (2). By the same token, halogens, phenylselenyl chloride, and the like add across the double-bond to give the corresponding compounds.

Figure 5:
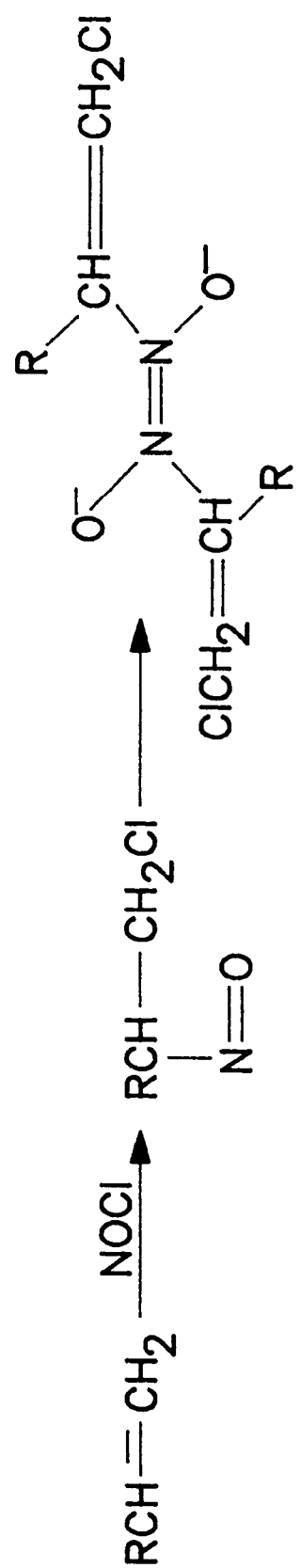
FIG. 5 shows addition of halogen-containing molecules across the double bond.

Other halogen-containing molecules may also undergo the same additions. As seen in FIG. 5, these additions allow the introduction of heteroatoms such as nitrogen and halogen to the double bond. As shown in FIG. 5, addition of nitrosyl chloride to the double bond gives the nitroso compound, that can be dimerized to give the stable oxime tautomer.

ii. Cycloaddition Reactions

Figure 6:
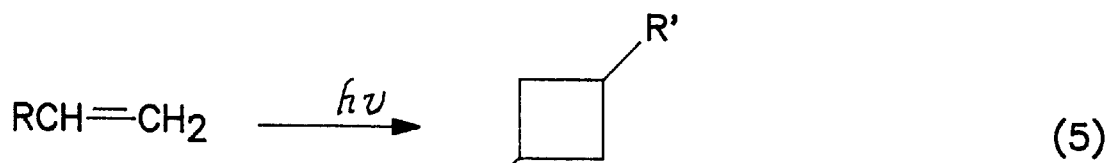
FIG. 6 shows cycloaddition reactions of olefins of α-allyl carboxylic acids.
Figure 6:
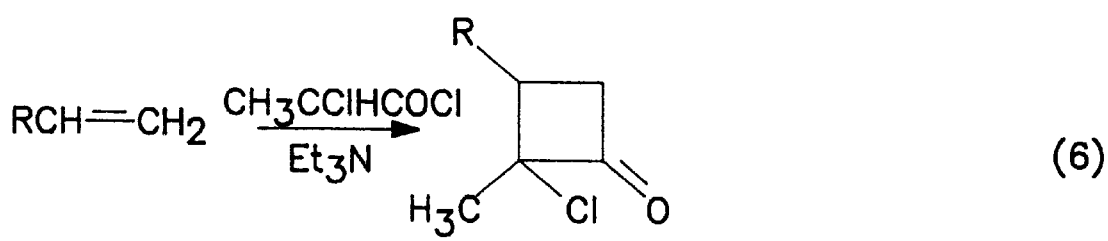
Figure 6:
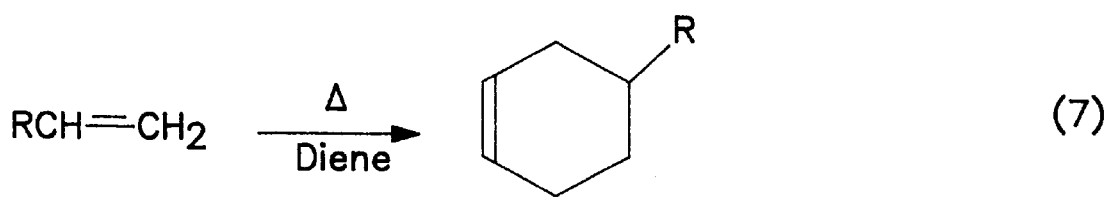
Figure 6:
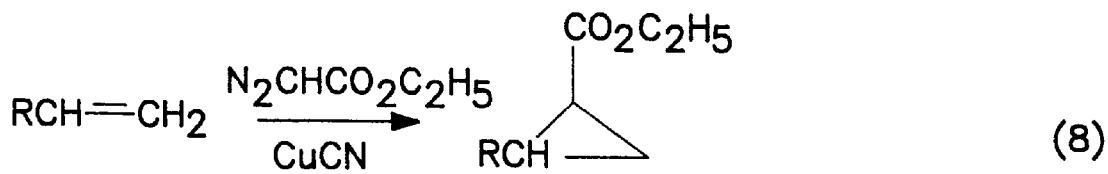
Figure 6:
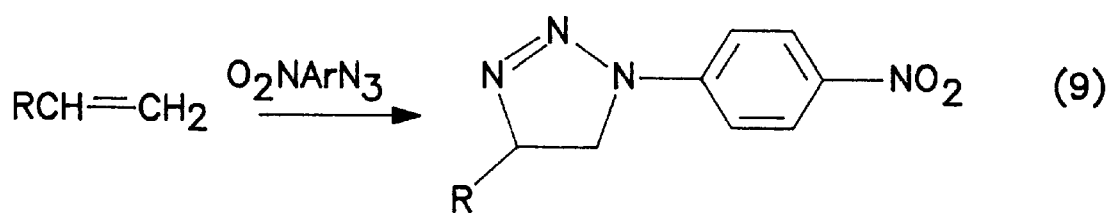

The α-allyl carboxylic acids, like all other alkenes, may undergo another typical olefin reaction, the cycloaddition. These reactions, as shown in FIG. 6, result in carbo- or hetero-cyclic (3, 4, 5 and 6 member) molecules. For instance, under photolytic conditions two alkenes may dimerize to form the cyclobutane (5); under thermolytic conditions, the alkene reacts with butadiene to give cyclohexene(7). The double bond of the α-allyl carboxylate also undergoes dipolar cycloadditions, examples are illustrated in FIG. 6 (6) and (9). The dipolar additions (to the double bond) bring about either the carbo-or heterocyclic compounds. The olefins also react with carbene (or nitrene) to afford cyclopropanes, such as the example given in FIG. 6 (8).

iii. Oxidation of the Carbon—Carbon Double Bond

Figure 7:
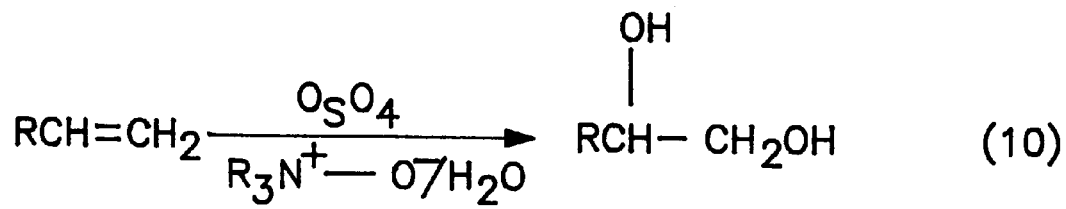
FIG. 7 shows oxidation of the carbon-carbon double bond of α-allyl carboxylic acids.
Figure 7:
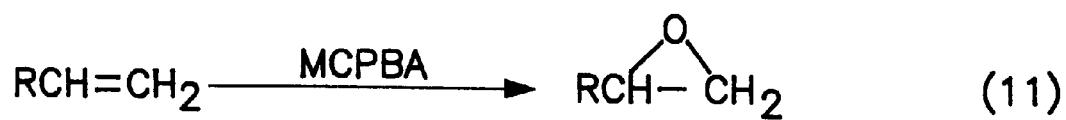
Figure 7:
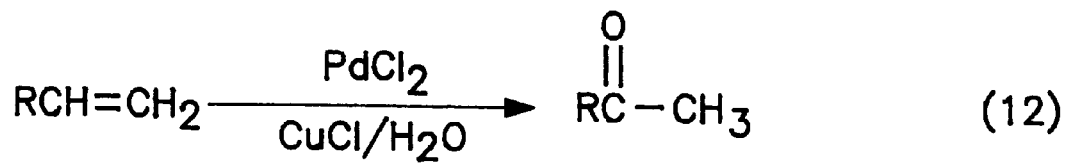
Figure 7:
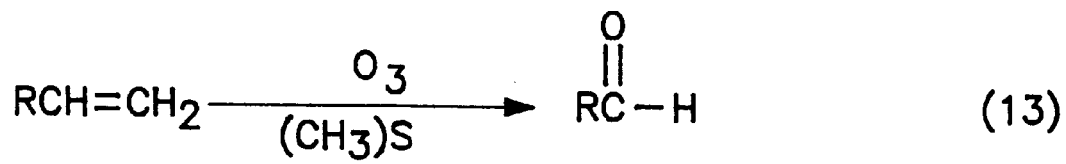

Oxidation of the double-bond that is a part of the α-allyl carboxylic acids can be achieved and affords different chemical products. Some selected oxidative reactions are listed in FIG. 7. For example, when the double-bond is treated with transition-metal oxides, such as $KMnO_4$, two oxygens, in the form of hydroxyls, are added across the double bond to give a diol (10); when treated with peroxide. $RCOOO^-$, one oxygen is added across the double bond to form an epoxide (11). The double-bond may be treated with Cu (I) salt in the presence of palladium chloride to afford a ketone (12). Last, the double bond may react with $O_3$, via an oxidative cleavage reaction, that results in the formation of an aldehyde (13).

B. Chemical Transformations Involving the Allylic System

Figure 8:
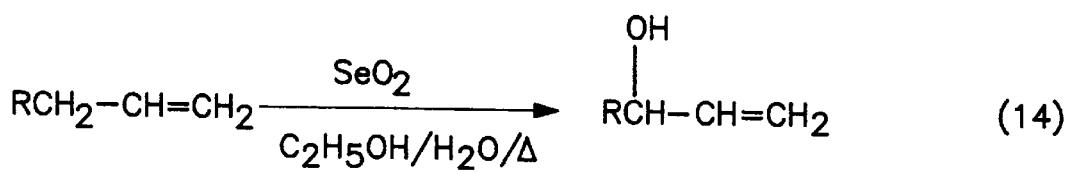
FIG. 8 shows transformations at the allylic carbon of α-allyl carboxylic acids.
Figure 8:
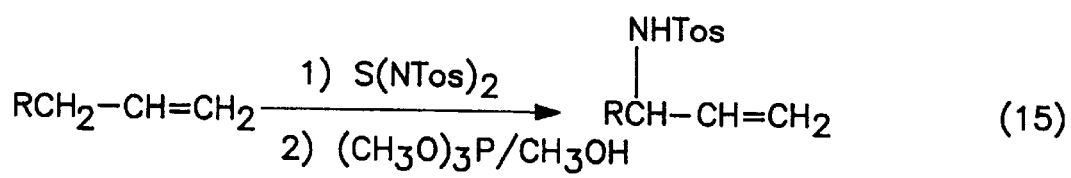
Figure 8:
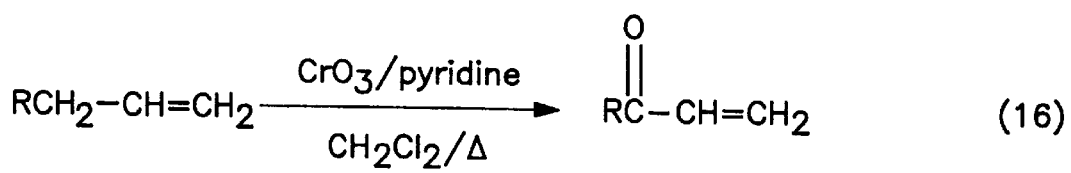
Figure 8:
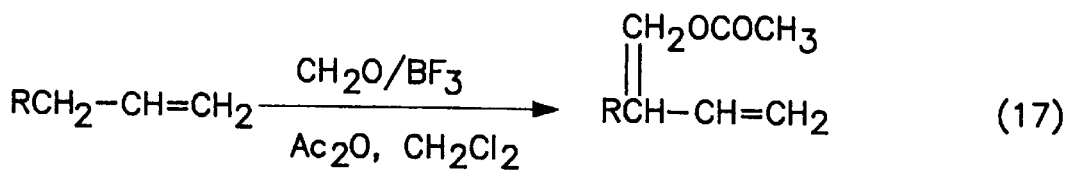
Figure 8:
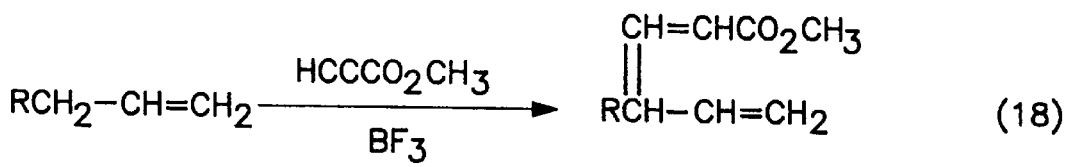

Aside from the chemical reactions directly related to the carbon—carbon double bonds, the allylic carbon (the carbon that is adjacent to the alkene) may undergo an unique set of conversions to afford different chemicals from those that result from the alkene transformations. Some examples are depicted in FIG. 8. An oxygen may be introduced either as a hydroxyl using $SeO_2$ (14) or as a carbonyl with Collin's reagents (16); these two products are, in fact, convertible via "redox" reactions. The amination of the allylic olefins can be effected using sulfur reagents, such as the one depicted in FIG. 8 (15). Lewis Acids, such as $BF_3$ may be used to afford allylic ene reactions, (17) and (18), to form new carbon—carbon bonds.

Figure 9:
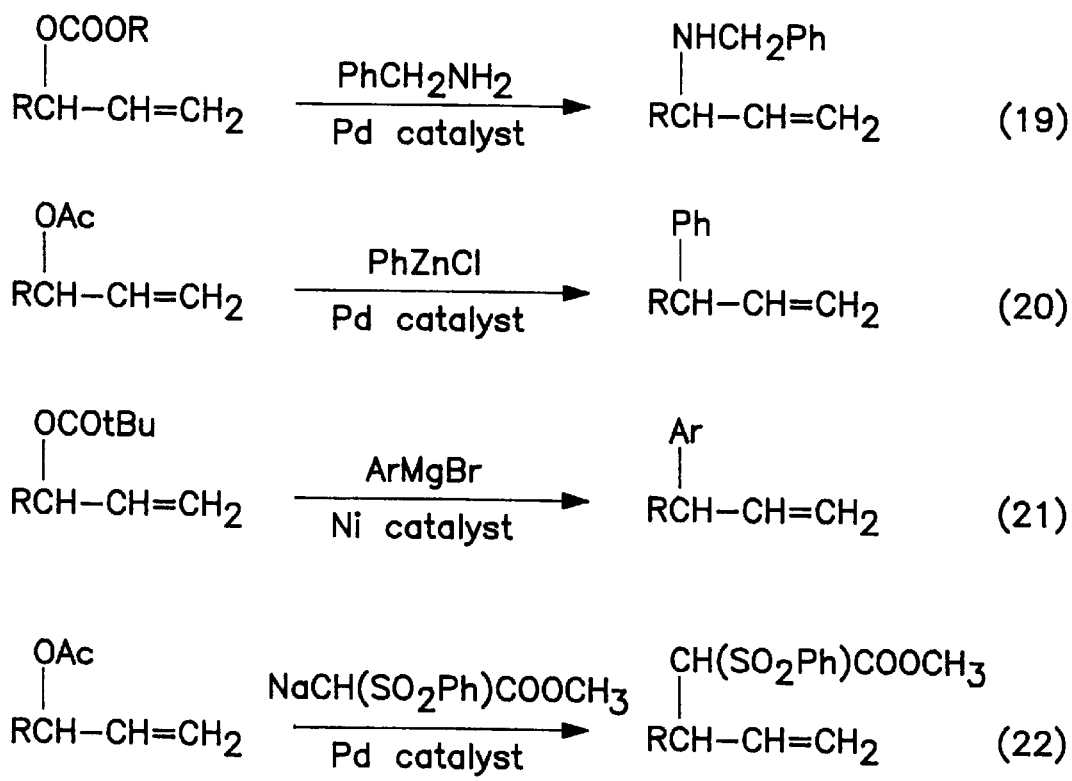
FIG. 9 shows nucleophilic displacement of allyl carbonate or the acetate.

Being activated by an allyl ester or a carbonate at the allylic position, the allylic is transformable to other functionalities when it forms a complex with transition metals, such as palladium and nickel. In FIG. 9, the allyl carbonate or the acetate can be displaced by an array of nucleophiles to afford a combination of different reaction products.

3. Preparation of Combinatorial Chemical Library Using Allylic Starting Materials and their Derivatives The α-allyl acids, esters, amides and their derivatives resulting from the alkene and allylic transformations may be employed as building blocks in making combinatorial compound libraries. The introduction of the allyl group to the acids and subsequent multiple simultaneous or parallel chemical transformations of the alkene and allylic functionalities introduce many different chemical functionalities in addition to the original carboxyl group itself. Therefore, many different chemical reactions may be used to assemble these small molecules into a library of compounds with higher molecular weights. These libraries may be constructed via a combinatorial array of chemical reactions. The reaction array for the assembly process may be monotonous resulting in linear oligomeric libraries. Alternatively, the array of reactions may not be repetitive, resulting in libraries which may be linear or branched compounds. Two examples of assembly processes are discussed below. The first example is the making of a peptide library. α-Allyl proline was used to make dipeptides on a solid phase with a common amino acid, lysine, to form both sequences (lysine-α-allyl proline and α-allyl proline-lysine). The second example is the making of a "trimeric" compound by linking an α-allyl valine to a dipeptide via the formation of cyclobutane by the pair of alkenes that were attached to both proline and valine. This example uses a combination of reactions utilizing the carboxyl and the alkene functionalities.

Figure 10:
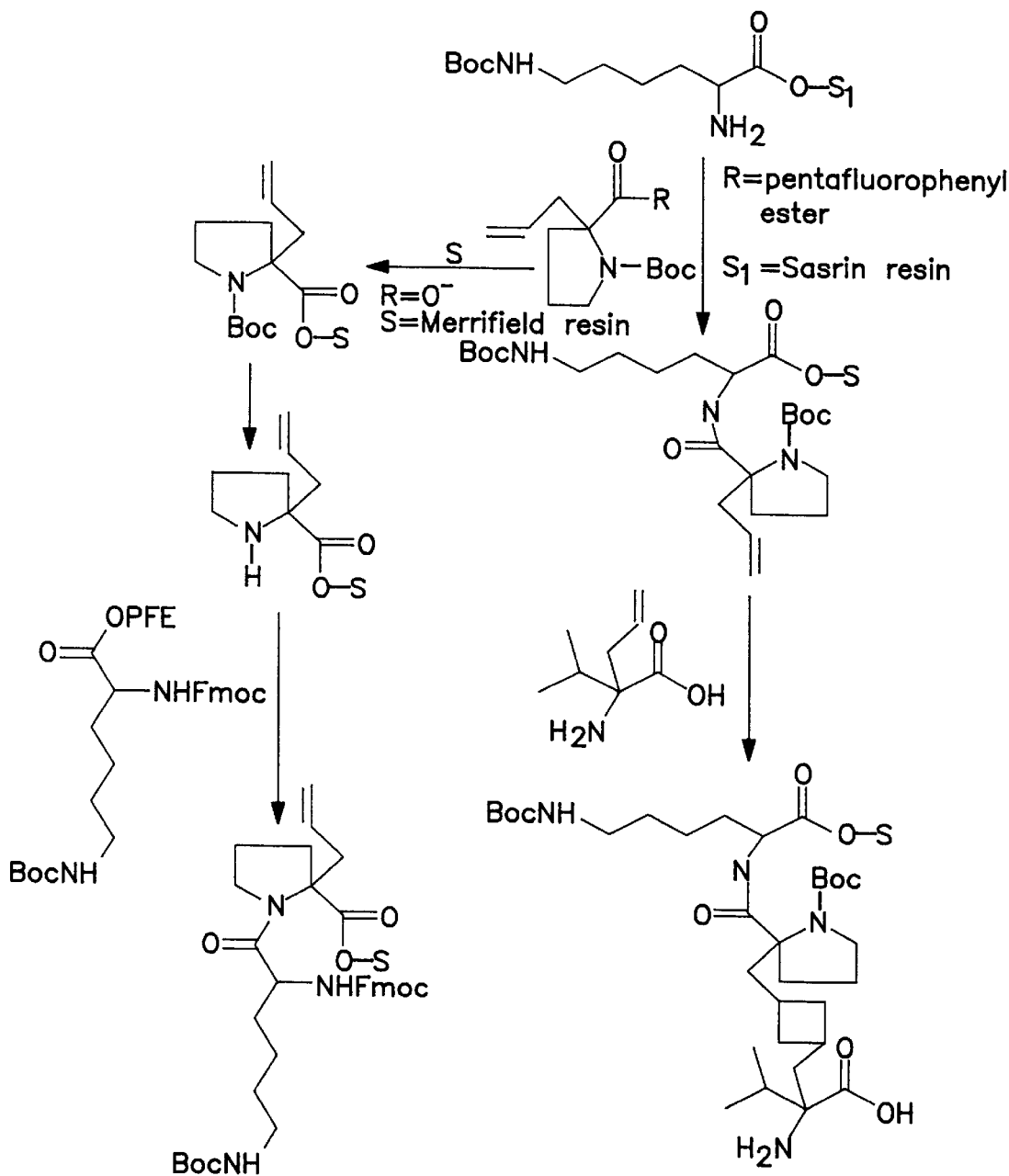
FIG. 10 shows the utilization of α-allyl carboxylates to form dimers and trimers.

As shown in FIG. 10, a dipeptide, ie., lysine-α-allyl-proline, is formed via an amide (peptide) linkage between the α-amino terminal of a lysine and the carboxyl terminal of an α-allyl proline. The dipeptide may be assembled (on a solid phase) using the conventional method of peptide synthesis, even though the amino acid residues are uncommon. The first-step of the reaction involves activating the carboxyl functionality of the α-allyl proline by formation of the pentafluorophenyl ester. The second-step prepares the α-amino terminal of lysine that is immobilized on a solid phase by removing the Fmoc-group under basic conditions, or the t-Boc group from the α-allyl proline. The two amino acids are then brought together to form a dipeptide, i.e., lysine-α-allyl proline (or α-allyl proline-lysine). This example demonstrates that the chemical transformation of the amino acids to new α-allyl amino acids does not alter the chemical reactivity of the acids themselves. Therefore, these acids may be used in conventional peptide synthesis. In the second reaction, another α-allyl amino acid is linked to the dipeptide using the alkene rather than the carboxyl functionality. In this case, the linkage formed between the α-allyl proline and the incoming α-allyl valine is by the formation of a cyclobutane ring via the pair of double bonds under photochemical reaction conditions. Thus, after the addition of the allylic functionalities and subsequent chemical transformations, these small molecular building blocks may be used to construct combinatorial libraries using a variety of chemical reactions.

4. Library Expansion By Library x Library Cross-Reactions

A library of compounds can react chemically with another library to afford a new and larger library with greater chemical diversity. Although not all libraries are reactive with one and another, a careful selection of different chemical libraries may allow a successful execution of such "library x library" expansion. In this section, a few of such options are discussed.

A. Cross Reaction of Allyl-Derivative Library with Peptide Library

Figure 11:
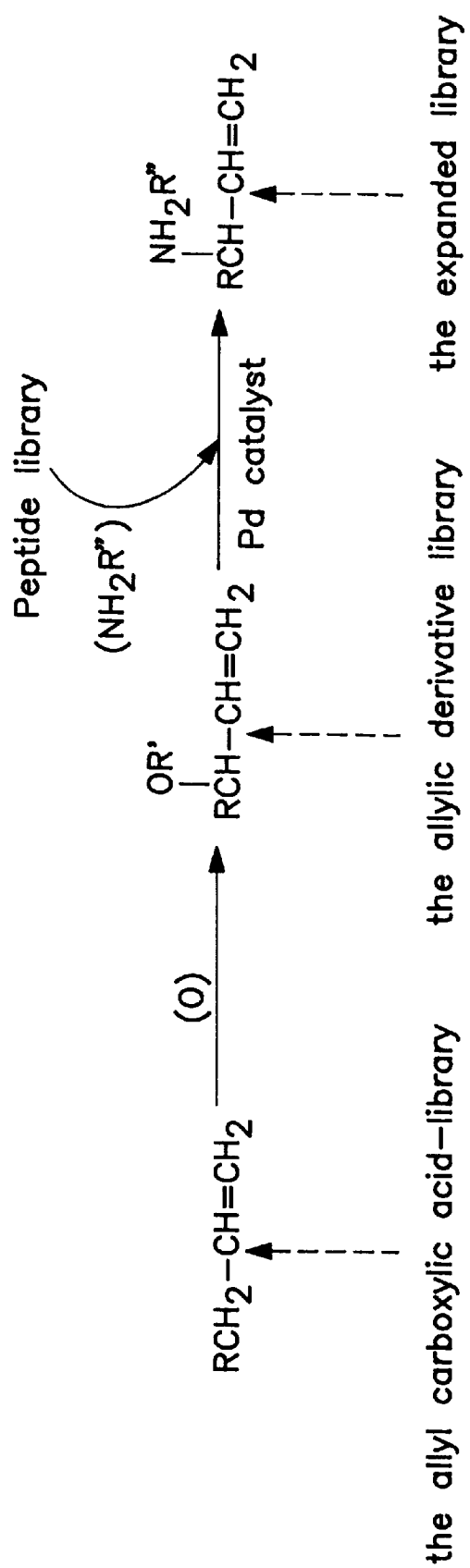
FIG. 11 shows a library containing alkyl carboxylic acids interacting with a peptide library.

Some of the allyl-derivative libraries may be brought to react with a standard peptide library using the chemical reaction illustrated above. As shown in FIG. 11, using the allylic transformation reaction depicted in FIG. 9, the allylic carbonate library (made by the allylic oxidation using $SeO_2$—FIG. 8, (1)), can be reacted with any peptide library, either linear or cyclic, as long as there is a free amino terminal. The N-terminal may be the N-terminal of a linear peptide, or an N-terminal of a cyclic peptide side chain.

B. Cross Reaction of Allyl-Derivative Libraries

Figure 12:
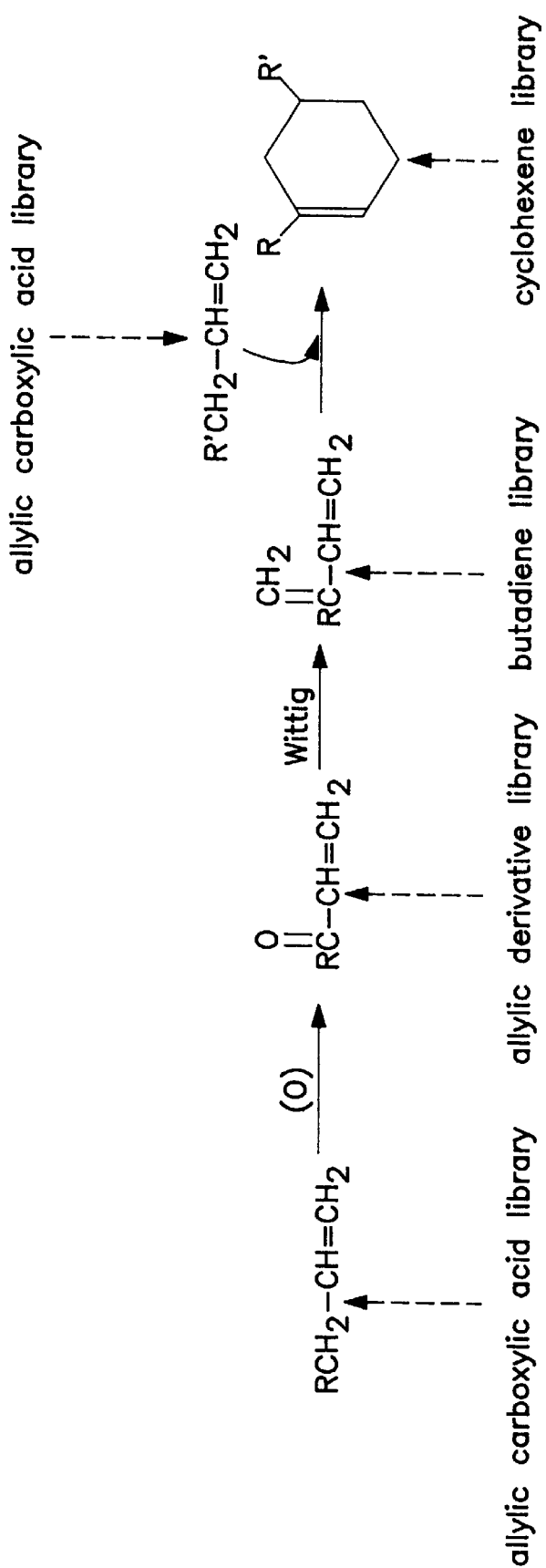
FIG. 12 shows the interaction of a diene library with an allyl carboxylic acid library to form a cyclohexene library.

Some of the allyl-derivative libraries are reactive with other allyl-derivative libraries under a given set of reaction conditions. For instance, the α-β unsaturated carbonyl, a conjugated system that is formed by allylic oxidation (FIG. 8), is a pivotal point of such a "library" expansion. With the conjugated system, many chemical transformations and interactions are possible. As shown in FIG. 12, by treating with a Wittig reagent, the allylics may be transformed to a library of butadienes. Consequently, any allyl library will be able to act as a dieneophile to react with a library of dienes to afford a new expanded library containing cyclohexane as the common molecular scaffold. An example of such a reaction is illustrated in FIG. 12.

5. Labeling of Lead Compounds and their Use

The primary goal and the ultimate object of this invention is to discover therapeutic agents. However, it as also a goal to discover potential lead compounds ("leads") from the collection of organic compounds. A lead that is identified from such a library of compounds may be used for further drug design. For instance, an individual lead identified (by a biological assay) from a library that is constructed with α-allyl α-amino acids, their derivatives, or fatty acids may be labeled with stable isotopes such as, but not limited to $^{13}C$, $^{15}N$, and/or $^{2}H$ by synthesis using α-amino acids (such as described in U.S. Ser. No. 08/493,300abandoned) or fatty acids which are enriched in a stable isotope. Such amino acids can be partially or completely labeled. A labeled individual compound when bound to a receptor may be used to map receptor structures using nuclear magnetic resonance spectroscopy (NMR). The conformation of the bound ligand reflects the receptor's binding structures. A better drug may be designed knowing such structures. The labeling of the library with radioactive isotopes using starting materials enriched in a radioactive isotope is also envisioned within the scope of the invention.

6. Kits for Preparing Chemical Libraries

Kits according to the present invention comprise two or more α-allyl carboxylic acids each in a separate physical compartment. Compartmentalization may be provided by packaging or solid phase attachments. The acids may have protecting or activating groups to facilitate subsequent transformations. Preferably written instructions are provided suggesting transformations, annelation, oligomerizations, etc. Ancillary reagents useful for such reactions may also be provided in the kits. Solid phase materials for performing library construction may also be provided.

7. Identification of Lead Compounds from Libraries

A. In Vitro Tests and Screenings

Any in vitro test may be used to identify lead compounds from multi-dimensional combinatorial libraries and to assess leads from these combinatorial libraries for their development potential. In vitro tests are often used as the primary assays by those who are skilled in the art of drug screening, discovery, and development to identify a lead of interest. Those assays may include, but are not limited to, a whole cell system, a cell-free system, and systems that use isolated organs or tissues. Several examples are described herein for illustration purposes only.

i. Whole Cell Test for Anti-Tumor Agents

Many different cell lines are available for anti-tumor drug screening. It is desirable, but not necessary to use human tumor cells for the assessments of the anti-tumor antibiotics. There are a number of cell culture media available. Any may be used which is appropriate for the cell line used for the tests.

a. Morphological changes (ref: Komiyama, K., and Funayama, S., Anti-tumor Agents in The Search for Bioactive Compounds from Microorganisms. Ed. by Omura, S., Brock/Springer Series in Contemporary Bioscience, pp88+, Springer-Verlag N.Y. (1992).)

A sample (a compound or a mixture of compounds) is added to the culture medium of tumor cells that are attached to the surface of a culture plate which is then incubated. Thereafter, cell are fixed and stained with dye (such as neutral red, Giemsa, crystal violet and tetrazolium) and morphological changes are observed. It is useful to compare the test substance with one or several known anti-tumor substances.

As an example, after trypsinization of HeLa cells to make a single suspension in MEM supplemented with 10% calf serum, $5 \times 10^3$ of the cells in 200 µl are plated into a 96 well microtiter plate. One day after cultivation at 37° C. under 5% $CO_2$ (95% air), 5 µl (at appropriate concentration, or a serial of dilution) of test sample is added to each well and the plates are re-incubated for another 2 to 3 days. The medium is removed by decantation and the plate is dipped into 100% methanol for more than 5 minutes to fix the cells. After the HeLa cells are washed with water, they are stained with a dye solution (such as 0.04% neutral red in HBSS), washed with water, and examined for morphological changes under the light microscope.

b. Determination of dye uptake(ref: Alley, M. C., Scudiero, D. A., Monks, A., Hursey, M. L., Czerwinskiu, M. J., Fine, D. L., Abbott, B. J., Mayo, J. G., Shoemaker, R. H., and Boyd, M. R., *Cancer Research* 589 48 (1988).) The appropriate cells are cultured, transferred, and treated with a test sample as described above. After the cells are exposed to the test sample 20 µl of the Tetrazolium solution (5 mg in 1 ml PBS) is added to each well and the plate is incubated at 37° C. for 4 h. After aspiration of the medium, 100 µl of 0.04 N HCl-IPA is added to each well and mixed. After 30–50 min. at room temperature, the plate is read on a microplate reader at 570 nm (630 nm ref.). In principle, the viable cell number per well is directly proportional to the production of formazan from tetrazolium.

ii. Cell-Free System for Enzyme Inhibition Assays

The test of inhibition of an enzyme (or of ligand binding to a receptor) may be carried out in a variety of different formats (ref: Nakamura, R. M., Kasahara, Y., and Rechnitz A. G. *Immunochemical Assays and Biosensor Technology for the 1990s*. American Society for Microbiology, Washington, D.C. (1992) and the references cited therein).

Two enzyme inhibition assays, inhibition of aldose reductase (for the prevention of late-onset cataract formation in diabetics) and inhibition of tyrosine-specific protein kinase (for inhibition of cancer development), are described below to illustrate this class of assays.

a. Aldose reductase (ref: Hayman , S., Kinoshita, J. H., *J. Biol. Chem.*, 877, 240 (1965).)

The lenses of calf eye are homogenized and centrifuged at 10,000×g for 15 min. The supernatant fluid is saturated with 50 to 75% of $(NH_4)_2SO_4$ to force the protein to precipitate. The precipitate obtained by another centrifugation is dissolved in 0.05 M NaCl and used as an enzyme preparation. Oxidation of NADPH to NADP+ (during the conversion of glucose to sobitol) is assayed by following UV adsorption at 340 mn with a spectrophotometer. The inhibition of the reductase activity is monitored by the absorbence changes ($A_{340\ nm}$) occurring during the reaction. A reaction mixture (3 ml) containing 100 mM phosphate buffer, pH6.0 , 0.04 mM NADPH, the enzyme preparation, and 0.5 mM DL-glyceraldehyde is incubated for 3 min. at 37 (C. The decrease of absorbence ($A_{340\ nm}$) is determined.

b. Tyrosine-specific protein kinase (ref: Umezawa, H., et. al. *J. of Antibiotics* 170, 39 (1986). ) The membrane fraction of the human epidermoid carcinoma cell line A-431 prepared by the method described by Thom et al. (ref.: Thom, D., Powell, A. J., Lloyd, C. W., and Reeds, D. A., *Biochemical J*. 187, 168 (1977)) can be used as an enzyme preparation. The reaction mixture, containing 1 mM $MnCl_2$, 10 ng of EGF, 40 mg of protein of the A-431 membrane fraction, 75 μg of albumin, 3 μg of histone and 20 mM HEPES buffer, pH 7.4, in a final volume of 50 μl, is pre-incubated for 10 min. in the presence and absence of the test sample. The reaction is then initiated by the addition of 10 μl of $[\gamma-^{32}P]$ ATP. After incubation for 30 min. at 0° C., an aliquot of the mixture (50 μl) is pipetted onto a Whatman filter paper and dropped immediately into a beaker of cold 10% TCA containing 0.01 M sodium pyrophosphate. The filter paper is washed with TCA solution, extracted with alcohol, and dried. The radio activity is measured by a scintillation counter.

B. In Vivo Tests and Screens

In vivo screening and in vivo efficacy evaluations are desirable, although not necessary for the identification and development of leads. Any in vivo test can be used as is appropriate for the desired activity. Although only anti-infective examples are described herein, the in vivo assessments of combinatorial libraries as well as of individual leads associated with a library should be conducted whenever possible.

i. Mouse protection test (ref: Richardson, K., Brammer, K. W., Marriott, M. S., and Troke, P. F. Antimicrob. Agents Chemother. 732, 27 (1985).)

The simplest type of anti-infective screening is a mouse protection test which was used in the discovery of fluconazole. Mice are infected intravenously with a lethal dosage (ca. $10^7$ yeast, death occurs within 48 hr. for untreated mice) of *C. albicans*. A group of five mice is treated orally or by injection with the test agent 1, 4, and 24 h after the infection. Mortality is assessed over 48 h. If several dosages are used, it is possible to calculate the 50% effective dosage ($ED_{50}$). In an initial screening situation, a single arbitrary dose (or the maximum tolerated dosage determined by the acute toxicity tests if conducted) may be used.

ii. Multiple infection test for orally active anti-infectives (Ref: (1) Ryley J. F., and Keith, B-B., *Screening for antifungal activity. Emerging Targets in Antibacterial and Antifungal Chemotherapy*. Ed by Sutcliffe J., and Georgopapadakou, N. H., pp546+; Routledge, Chapman and Hall Inc. N.Y., N.Y., (1992).)

Female mice, previously treated with estradiol, are infected with *C. albicans* in the vagina and *T. mentagrophytes* var quinckaenum on the back. The infected mice are fed orally with the test compound or compounds at a dosage ca. 250 mg/kg once daily for 5 days. Infection is assessed on day 6 or 7. Ringworm lesions are scored visually, and vaginal infections are monitored by plating out a sample with a wire loop onto BiGGY agar (Difco) and scoring growth upon incubation.

EXAMPLES

Example I

Preparation of α-allyl valine: Valine hydrogen chloride methyl ester (6.51 g, 33.9 mmol) was suspended in toluene (ca. 200 ml dried with 4 Å molecular sieve) in a reaction flask (250–300 ml). To the suspension, benzaldehyde (2 m equiv.) and toluenesulfonic acid (monohydrate, cat. amount, ca. 200 mg) were added. The flask was equipped with a Dean-Stark trap, that was charged with freshly flamed-dried 4 Å molecular sieves and a refluxing condenser that was connected to a Drierite filled tube. The reaction was heated to reflux. After every 24 hr of refluxing, the 4 Å molecular sieves in the Dean-Stark trap were re-charged with fresh ones (after the reaction was cooled to room temperature) for a total of 78 hrs. The reaction mixture was then cooled to room temperature and partitioned between $H_2O$ (300 ml) and $CH_2Cl_2$(300 ml). The layers were separated. The organic layer was then washed with $NaHCO_3$ (sat. eq. vol.×3) and NaCl (sat., eq. vol.×2). Then, the organic solution was dried with anhydrous $Na_2SO_4$ for 25 to 30 minutes, filtered and concentrated in vacuo. The preparation was left under vacuum for 24 hrs and the concentrate was resuspended with additional $CH_2Cl_2$. The evaporation and concentration process were repeated three times in order to remove the aldehyde residue and to afford a clear, transparent, oily N-benzylideneamine amino acid methyl ester (6.57 g, 93.2%) with very little aldehyde contamination.

N-benzylideneamine valine methyl ester (6.0 g, 28.8 mmol) was dissolved in THF (ca. 200 ml; freshly distilled over Na/benzylphenone, and transferred with a double-ended-needle) and cooled to −78° C. with a dry-ice/acetone bath. LDA (1.1 meq, a solution in cyclohexane) was added to the solution, dropwise. The solution was then stirred at the above temperature under Ar for ca 1 hr. To the solution, allylbromide (2 meq) was added along with HMPA (10 ml). The temperature was brought to ambient, and the reaction was stirred under Ar for 12 hrs. $CH_3OH/H_2O$ (10 ml, 1:1) was added to the reaction mixture, that was partitioned between t-butyl methyl ether (250 ml) and $H_2O$ (150 ml). The layers were separated. The organic layer was then washed extensively with $H_2O$ (eq. vol.×5), which was concentrated under reduced pressure. The concentrate was suspended in $CH_3OH$/TFA(aq. 50%, v:v) and stirred at room temperature for ca. 24 hr. The solution was partitioned between t-butyl methyl ether (200 ml) and $H_2O$ (200 ml). The layers were separated, and the organic layer was washed with additional $H_2O$ (eq. vol.×1). The aqueous layer was combined and washed with additional t-butyl methyl ether (eq. vol.×2). The aqueous solution was then freeze-dried to give the A-allyl valine (3.93 g 92.8%) a light tan, amorphous solid Example II Preparation of α-allyl benzyldeneamine phenylalanine ethyl ester L-Phenylalanine ethyl ester hydrochloride (1.0 g, 4.36 mmol) was dissolved in toluene (ca. 125 ml dried with 4 Å molecular sieves). To this solution, benzaldehyde (1.5 m equiv.) and p-toluene sulfonic acid monohydrate (ca. 50 mg) was added. The solution was refluxed in a Dean-Stark apparatus charged with dried 4 Å molecular sieves. The system was closed from outside moisture. After refluxing for 6 h, the reaction contained almost no starting material by TLC. The reaction mixture was allowed to cool to room temperature, and then poured into a beaker containing ice-water (ca. 300 mL) with a few drops of 0.1 N HCl and TBME (ca.300 mL). The TBME layer was collected and the aqueous layer was treated with another 100 mL of TBME. The TBME extracts were combined, washed with brine water (sat'd. NaCl ca. 150 mL), and dried over anhydrous sodium sulfate. The sodium sulfate was filtered off and the TBME was removed under reduced pressure. The yield of product, benzyldeneamino phenylalanine ethyl ester, obtained after drying 24 h under vacuum was 0.891 g (ca. 73%).

Syrupy reaction product (891 mg, 3.16 mmol) was dissolved in dry THF (ca. 90 mL). This solution was cooled to −78° C. and flushed with argon. LDA (3.16 mL, 1.5 M in cyclohexane) was added slowly and the mixture was stirred for 1 h. Allyl bromide (410 μL, 4.74 mmol) was added to the mixture. After 15 min. HMPA (1 mL) was added to the reaction. The reaction mixture was allowed to warm to room temperature slowly. After stirring for 24 h, the reaction mixture was partitioned between ice-water (ca. 300 ml) and TBME (ca. 300 ml). The TBME layer was collected and washed twice with water (ca. 200 ml). The TBME layer was dried over anhydrous sodium sulfate. The solution was filtered and concentrated under reduced pressure; then dried for 24 h under vacuum to yield α-allyl benzyldeneamino phenyl ethyl ester (924 mg, 2.88 mmol; 91% yield; t.l.c. $R_f$=0.6 hexane: TBME 4:1).

Example III

Preparation of N-t-Boc N-pMBn, α-allyl glycine: N-t-Boc glycine methyl ester (5 grams, 26.5 mmol) was dissolved in DMF (ca. 150–200 ml). The solution was then cooled with a salt/ice bath to ca. 5° C. while the NaH (previously washed with hexane and ether, and dried under vacuum, 1.1 meq) was added portionwise via a solid addition-funnel. The suspension was then stirred at the above temperature under Ar for 1 hr. p-methoxybenzylchloride (ca. 1.2 meq) was added dropwise to the slurry while the reaction was cooled with the ice bath. The reaction temperature was slowly raised to ambient when the ice slowly melted. The reaction mixture was stirred at room temperature under Ar for 12 to 16 hr. Approximately 50% of the DMF used was removed under reduced pressure with a rotary-evaporator equipped with an vacuum-pump. The concentrated solution was partitioned with $CH_2Cl_2$ (200–300 ml) and $H_2O$ (200–300 ml). The layers were separated, and the aqueous layer was extracted once more with additional $CH_2Cl_2$ (eq. vol.×1). The combined organic layers were washed sequentially with $H_2O$ (eq. vol.×2), HCl (0.1 N, eq. vol.×2), $NaHCO_3$ (sat. eq. vol.×2) and NaCl (sat., eq. vol.×1). Then, organic layer was dried with anhydrous $Na_2SO_4$ for 25 to 30 minutes, filtered and concentrated in vacuo to give the crude material (containing a trace amount of p-methoxybenzyl alcohol and starting amino acids). The purified material was obtained by silica gel (70–230 mesh) flash column chromatography with t-butyl methyl ether/hexane (1:4) as the mobile phase. N-Boc N-p-MBN glycine methyl ester was recovered from the column as a lightly tan colored solid (4.28 g, ca. 52.3%)

N-Boc N-p-MBn glycine methyl ester (2.0 g, 6.5 mmol) was dissolved in THF (ca.100–150 ml, freshly distilled over Na/benzylphenone and transferred with a double-ended needle) and cooled to −78° C. with a dry-ice/acetone bath. To the reaction, LDA (1.1–1.2 meq) was added, dropwise, under Ar. The solution was then stirred under this condition for ca. 1 hr. Allylbromide (2 m equiv.) was added dropwise while the reaction was maintained at the above conditions. HMPA (ca. 10 ml) was added to the reaction thereafter. The temperature of the reaction, while under Ar, was slowly elevated to ambient over 2 hr. The mixture was stirred at ambient temperature under Ar for another 16 hr. The solution was partitioned between t-butyl methyl ether (ca. 200–250 ml) and $H_2O$ (200–250 ml). The layers were separated. The organic layer was washed extensively with $H_2O$ (200 ml or eq. vol.×6), HCl (0.1 N, eq. vol.×2), $NaHCO_3$ (sat. eq. vol.×2) and NaCl (sat., eq. vol.×1). Then, the organic solution was dried with anhydrous $Na_2SO_4$ for about 25 to 30 minutes, filtered and concentrated in vacuo to give a crude product containing mainly the allyl amino acid methyl ester and trace amounts of starting material with others components that were not characterized. The purified material was obtained by silica gel (70–230 mesh) flash column chromatography with t-butyl methyl ether/hexane (1:10) as mobile phase. The purified ester was suspended in $CH_3OH$ (ca. 50 ml) and an aqueous solution of NaOH was added (aq. 1N, ca. 30–50 ml). The solution was stirred at room temperature for 4 hr., then partitioned between t-butyl methyl ether (150 ml) and water (150 ml). The layers were separated with a separatory funnel. The organic layer was washed with additional NaOH (aq., eq. vol., 0.1 N×1). The basic aqueous layers were combined and back-washed with additional t-butyl methyl ether (eq. vol×1). The aqueous solution was then titrated to pH 2 with HCl (aq. 3N). The resultant organic acid was extracted with $CH_2Cl_2$ (eq. vol.× 5). The combined organic extracts were dried with anhydrous Na₂SO4, filtered, and concentrated in vacuo to give the corresponding allyl amino acid (1.67 g, 76.4% ).

Preparation of N-t-Boc N-pMBn. α-allyl threonine: N-t-Boc, O-Bn threonine methyl ester (2 grams, 6.5 mmol) was dissolved in DMF (ca. 150–200 ml). The solution was then cooled with a salt/ice bath to ca. 5° C. while the NaH (previously washed with hexane and ether, and dried under vacuo, 1.1 meq) was added portionwise via a solid addition-funnel. The suspension was then stirred at the above temperature under Ar for 1 hr. p-methoxybenzylchloride (ca. 1.2 meq) was added dropwise to the slurry while the reaction was cooled with the ice bath. The reaction temperature was slowly raised to ambient when the ice slowly melted. The reaction mixture was stirred at room temperature under Ar for 12 to 16 hr. Approximately 50% of the DMF used was removed under reduced pressure with a rotary-evaporator equipped with an vacuum-pump. The concentrated solution was partitioned with $CH_2Cl_2$ (200–300 ml) and $H_2O$ (200–300 ml). The layers were separated, and the aqueous layer was extracted once more with additional $CH_2Cl_2$ (eq. vol×1). The combined organic layers were washed sequentially with $H_2O$ (eq. vol.×2), HCl (0.1 N, eq. vol.×2), $NaHCO_3$ (sat. eq. vol.×2) and NaCl (sat., eq. vol.×1). Then, organic layer was dried with anhydrous $Na_2SO_4$ for 25 to 30 minutes, filtered and concentrated in vacuo to give the crude material (containing a trace amount of p-methoxybenzyl alcohol and starting amino acids). The purified material was obtained by silica gel (70–230 mesh) flash column chromatography with t-butyl methyl ether/hexane (1:4) as the mobile phase. N-Boc N-p-MBn threonine methyl ester was recovered from the column as a tan colored solid (1.12 g, ca. 40%)

N-Boc N-p-MBn threonine methyl ester (1 g, 2.3 mmol) was dissolved in THF (ca. 100–150 ml, freshly distilled over Na/benzylphenone and transferred with a double-ended needle) and cooled to −78° C. with a dry-ice/acetone bath. To the reaction, LDA (1.1–1.2 meq) was added, dropwise, under Ar. The solution was then stirred under this condition for ca. 1 hr. Allylbromide (2 m equiv.) was added dropwise while the reaction was maintained at the above conditions. HMPA (ca. 10 ml) was added to the reaction thereafter. The temperature of the reaction, while under Ar, was slowly elevated to ambient over 2 hr. The mixture was stirred at ambient temperature under Ar for another 16 hr. The solution was partitioned between t-butyl methyl ether (ca. 200–250 ml) and $H_2O$ (200–250 ml). The layers were separated. The organic layer was washed extensively with $H_2O$ (200 ml or eq. vol.×6), HCl (0.1 N, eq. vol.×2), $NaHCO_3$ (sat. eq. vol.×2) and NaCl (sat., eq. vol.×1). Then, the organic solution was dried with anhydrous $Na_2SO_4$ for about 25 to 30 minutes, filtered and concentrated in vacuo to give a crude product containing mainly the allyl amino acid methyl ester and trace amounts of starting material with others components that were not characterized. The purified material was obtained by silica gel (70–230 mesh) flash column chromatography with t-butyl methyl ether/hexane (1:10) as mobile phase. The purified ester was suspended in $CH_3OH$ (ca. 50 ml) and an aqueous solution of NaOH was added (aq. 1N, ca. 30–50 ml). The solution was stirred at room temperature for 4 hr., then partitioned between t-butyl methyl ether (150 ml) and water (150 ml). The layers were separated with a separatory funnel. The organic layer was washed with additional NaOH (aq., eq. vol., 0.1 N×1). The basic aqueous layers were combined and back-washed with additional t-butyl methyl ether (eq. vol×1). The aqueous solution was then titrated to pH 2 with HCl (aq. 3N). The resultant organic acid was extracted with $CH_2Cl_2$ (eq. vol.× 5). The combined organic extracts were dried with anhydrous $Na_2SO4$, filtered, and concentrated in vacuo to give the corresponding allyl amino acid (0.835 g, 77.4%). α-allyl histidine was made using identical reaction conditions and the product recovery was compariable to the above ones discussed.

Example IV

Preparation of α-allyl proline: t-Boc proline (10 grams, 46.5 mmol) was dissolved in nearly 100 ml of DMF along with 1.1 meq of $K_2CO_3$ (1.1 meq). The solution was stirred at room temperature under Ar for 1 hr. Allyl bromide (1.1 meq) was then added to the solution dropwise at room temperature under Ar. After addition, the mixture was stirred under the same conditions for 16 hr. DMF (60 to 80% of the total volume) was removed under reduced pressure with a rotary evaporator. The resultant slurry was partitioned with $CH_2Cl_2$ (250–300 ml) and $H_2O$ (eq. vol.). The organic layer was then separated with a separatory funnel; the aqueous layer was washed with additional $CH_2Cl_2$ (eq. vol.×1). All organic extracts were combined. The combination was washed sequentially with $H_2O$ (eq. vol.×2), HCl (0.1 N, eq. vol.×2), $NaHCO_3$ (sat. eq. vol.×2) and NaCl (sat., eq. vol.×1). Then, the organic solution containing only the esters (and maybe a trace amount of DMF) was dried with anhydrous $Na_2SO_4$ for 25 to 30 minutes, filtered and concentrated in vacuo to give the esters (11.72 g) in ca. 99% yield.

t-Boc proline allyl ester (2 g, 7.84 mmol) was dissolved in THF (ca. 150–175 ml, freshly distilled over Na/benzophenone). The solution was cooled to −78° C. with a dry-ice/acetone bath under Ar. To the solution, LDA (1.1 meq) was added dropwise. The solution was stirred under Ar at −78° C. for ca. 1 hr. Trimethylsilylchloride (1.1–1.2 meq) was added dropwise. The temperature was maintained at −78° C. for another hour before withdrawing the bath, then, raised to ambient for the next 2 hr., then again brought to reflux (THF) for another 3 hr. The reaction mixture was then allowed to cooled to ambient before the addition of $CH_3OH/H_2O/AcOH$(1:1:trace). The mixture was stirred for another 40 min. at ambient. The solution was partitioned between $CH_2Cl_2$ (150 ml) and $NaHCO_3$ (sat. 150 ml). The organic layer was then extracted once with the base (this organic layer contained the remaining of the starting material which may be used to make additional amounts of α-allyl amino acids). The combined aqueous extracts was then back-washed with $CH_2Cl_2$ (ca. 200 ml×1). The basic aqueous solution was triturated rapidly to pH 2 with HCl (3N). The organic acid in the aqueous suspension was immediately extracted with $CH_2Cl_2$ (eq. vol.×5). All organic extracts were combined. The combined extract was back-washed with $H_2O$ (eq. vol.×1) and NaCl (sat. eq. vol.×2), then dried over $Na_2SO_4$, filtered, and concentrated in vacuo to give a clear oil (0.947 g, 47.4% yield) that became an amorphous solid upon standing.

Example V

α-propylacetone -t-Boc-proline methyl ester A solution of $PdCl_2$ (54 mg, 0.303 mM) and CuCl (300 mg, 3.03 mM) in $DMF:H_2O$ (7:1, 30 ml) was stirred at room temperature. The mixture was kept under an oxygen atmosphere, while a solution of α-allyl-proline methyl ester in $DMF:H_2O$ (7:1, 20 ml) was added. The reaction was heated to 60° C. and stirred for 6 hr. After 6 hr., the reaction mixture was partitioned between t-butyl methyl ether (TBME) and water. The organic layer was collected and the aqueous layer was extracted with additional t-butyl methyl ether (eq. vol.×3). The organic extracts were combined and washed with water (eq. vol.×1) dried over $Na_2SO_4$, then filtered. The filtrate was concentrated in vacuo to give an oil which was then purified using silica gel flash column chromatography (Hexane: EtOAc=4:1) to give the corresponding methyl ketone in ca. 80% yield. The initial proton NMR analysis of the crude reaction product(s) indicated that ca. 6% of the oxidative product was the corresponding aldehyde which was not included in the recovered products after purification.

Example VI

Preparation of hydroxyl-allyl t-Boc proline (an allylic oxidation reaction) α-allyl-t-Boc-proline (128 mg, 0.50 mmol) was dissolved in $C_2H_5OH$ (95%, ca. 200 ml) with $SeO_2$ (1.01 eq.). The solution was refluxed for ca. 16 hr. under nitrogen then cooled to ambient. The solution was then partitioned between HCl (aq. 1N, 100 ml) and t-butyl methyl ether (100 ml). The layers were separated and the aqueous was washed with additional t-butyl methyl ether. The combined organic extract was washed with $H_2O$ (eq. vol.×2), $NaHCO_3$ (aq. sat., eq. vol.×2) and NaCl (sat. eq. vol.×1); dried over $Na_2SO_4$ for 25–30 min., filtered, and concentrated in vacuo to give a lightly tan solid. TLC analysis indicated a mixture of the oxidation product was obtained. The mixture of the allylic oxidative products were separated using silical gel chromatography which was eluted with a step gradient of chloroform/methanol (100:0; 90:10; v:v). The first fraction was collect as the δ-lactone (42 mg, ca. 30%), the second fraction was the recovered starting material (ca. 27.2 mg, 21%) and the last fraction was the hydroxyl allylic hydroxylated derivative (35 mg, 26.2%). Other components in the reaction mixture that were tightly bonded to the column origin that were not eluted.

Example VII

Preparation of α-propyleneoxy N-t-Boc proline (olefin oxidation with N-protected amino acid) α-allyl -N-t-Boc proline (150 mgs, 0.59 mmol) was dissolved in NaOH (aq. 2N, 50 ml) in a 250 ml reaction flask. The reaction temperature was maintained at ambient with a water bath. Hydrogen peroxide (30%, 40 eq) was added to the reaction portionwise over 48 hr. The reaction mixture was then partitioned between HCl (1N 150 ml), t-butyl methyl ether (200 ml) and crushed ice (50 ml, packed). The organic layer was separated from the aqueous. The aqueous was washed with additional t-butyl methyl ether (eq. vol.×1). The organic was then combined, dried with $Na_2SO_4$ (anhydrous), filtered, and concentrated in vacuo to give an colorless oil. The reaction product and starting material was separated using silica gel chromatography (chloroform:methanol= 10:1) to afford the purified epoxide (ca. 58 mg) in ca. 36.6% yield. Nearly half of the starting material (78 mg, 52%) was also recovered.

Example VIII

Preparation of α-propyloxy valine (olefin oxidation with unprotected amino acid) α-allyl valine (the free amino acid, 810 mg, 5.16 mM) was dissolved in CH₃OH/NaOHaq (100 ml, 1:1; NaOH 1N, aq). The peroxide, m-chloroperoxybenzoic acid (1.1 eq), was added to the solution and the reaction was stirred at ambient temperature for 2 hr. The basic solution was rapidly neutralized with TFA (aq. 50%, v:v) to pH 2. The acidic aqueous solution was washed with t-butyl methyl ether (to remove the MCPBA and benzoic acid, eq. vol×5) and the aqueous was freeze-dried to give the epoxide. The TLC analysis (silica/Butanol:AcOH:H₂O, 4:1:1) of the aqueous solution indicated that the conversion was qualitative and no starting material was observed from either the chromatography analysis or the NMR analysis of the resultant product.

Example IX

Preparation of Lysinyl-α-allyl proline (Merrifield method) α-allyl t-Boc-proline (556 mg, 2.18 mmol) was suspended in DMF (50 ml). NaH (ca. 55 mg; 1 m equiv.) was then added to the suspension. The suspension was stirred at room temperature for 1 hr. Merrifield resin (25 mg, chloromethyl resin) was added to the suspension. The suspension was heated on an oil bath for 16 hr. at 80° C. with occasional shaking, after which the slurry was cooled to room temperature and filtered. The collected resin was rinsed extensively with DMF. then placed in a reaction 10 ml vial (with a V-shaped stirring bar) and treated with 10% TFA in CH₂Cl₂ for 20 min. at room temperature. The resin was again harvest by filtration, and rinsed with TEA in CH₂C₂ (10%, v:v). The resin was re-suspended in the reaction vial in DMF (5 ml). To the vial was then added ε-N-t-Boc, α-N-Fmoc lysine pentafluorophenyl ester (50 mg in a 4 ml DMF suspension). The resultant suspension was stirred at room temperature for 4 hrs. The resin (with the dipeptide) again harvest by filtration and rinsed extensively with DMF and dichloromethene. The dipeptide was then removed by treating the resin with HBr-TFA. The TLC analysis (C₁₈/CH₃CN: 1% TFA aq., 60:40; v:v) indicated the formation of a dipeptide which was visualized by the aniline/sulfuric spray.

Example X

Preparation Valinyl-α-cyclobutane-prolinyl-lysine α-allyl-t-Boc proline (500 mg 1.96 mmol) was dissolved (in a 50 ml flask with a 14/20 joint) in freshly distilled THF (50 ml) and a THF solution of pentafluorophenol (1.1 m equiv.) was added va a double end needle. The solution was stirred and cooled in an ice bath and a THF solution of dicyclohexylcarbodiimide (1.1 m equiv.) was added via another double-ended needle. The reaction mixture was then stirred for about 1 hr in the ice-bath and another 3 hr. at room temperature.

ε-t-Boc α-Fmoc lysinylsasrin resin (ca. 50 mg) was suspended in piperidine (50 ml, 20% in DMF, v:v) for about 1 hr with gentle shaking on a shaker. The resin was then harvested by filtration, rinsed with additional DMF (10 ml×3), and placed in a 50 ml reaction flask (with a 14/20 joint), and re-suspended with another 25 ml of DMF. To this slurry was added the above activated prolinyl ester via a shlenck filter (to remove the dicyclohexylurea precipitate). Upon the addition, the reaction was sealed under Ar. The resultant reaction suspension was gently shaken at room temperature over night. The resin was again harvested by filtration, rinsed extensively with THF (20 ml×5) and DMF (ca. 20 ml×5).

The above α-allyl t-Boc-prolinyl lysinyl sasrin resin (30 mg) was then suspended in 100 ml of methanol (aq. 70%, v:v) and placed in a photochemical reactor which was purged with Ar. α-allyl valine (500 mg) was added to the solution. The reaction was the irradiated with a mid-pressure xxx lamp for ca. 25 min. Another batch of α-allyl valine (ca. 250 mg) was again added to the reaction. The reaction was then again radiated for another 35 min. The resin was harvest by filtration, rinsed with H2O/methanol (50:50, v:v).

Both dipeptide and the trimeric compound is removed from the resin by treating the resin with TFA (in CH₂Cl₂) and analyzed with TLC. The TLC analysis(visualized by the aniline/sulfuric spray )of the dipeptide (C₁₈/CH₃CN: 1% TFA aq., 60:40; v:v) indicated the complete formation of a dipeptide, which was the corresponding α-allyl t-Boc-prolinyl lysine. Whereas the other is a mixture of the starting dipeptide and a trimeric component corresponding to the tittle compound.

BIBLIOGRAPHY

1. Houghten, *Current Biology* 4:564–567 (1994)
2. Houghten, U.S. Pat. No. 4,631,211
3. Houghten et al., *Nature* 354:84–86 (1991)
4. Nikolaiev et al., *Peptide Research* 6:161–170 (1993)
5. Ostresh et al., *Proc. Natl. Acad. Sci. USA* 91:11138–42 (1994)
6. Salmon et al., *Proc. Natl. Acad. Sci.* 90:11708–12 (1993)
7. Simon et al., *Proc. Natl. Acad. Sci.* 89:9367–71 (1992)
8. Wang et al., *Biochemistry* 32:11285–92 (1993)
9. Zuckerman, *Current Opinion in Structural Biology* 3:580–584 (1993)
10. Zuckerman, *J. Am. Chem. Soc.* 114:10646–47 (1992)

What is claimed is:

1. A method of making a combinatorial chemical library, comprising the step of:

converting in parallel a set of at least two different α-allyl carbonyl monomers to form monomer derivatives, the monomers having a structure

$R^1R^2C(CR^4R^5—CR^6=CR^7R^8)—COR^3$ wherein $R^1$ and $R^2$ are independently H, alkyl, aryl, carbocyclic, heterocyclic, or chemical moieties comprising one or more atoms of O, N, S, X, or P, wherein X is halogen;

$COR^3$ is an amide, an ester, or a carboxyl group; and $R^4$–$R^8$ are independently H, aryl, or alkyl;

wherein the step of converting comprises converting the allyl functionality $—(CR^4R^5—CR^6=CR^7R^8)$ of the monomers to a structurally distinct functionality such that the set of monomers having converted allyl functionalities form a combinatorial chemical library, said method further comprising the step of covalently linking at least two monomers to form oligomers, wherein the monomers are selected from the group consisting of the at least two different α-allyl carbonyl monomers and the monomer derivatives thereof wherein the said oligomers contain at least two monomers linked through an heteroatom.

2. A method of making a combinatorial chemical library, comprising the step of:

converting in parallel a set of at least two different α-allyl carbonyl monomers to form monomer derivatives, the monomers having a structure

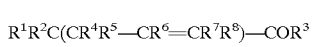

$R^1R^2C(CR^4R^5—CR^6=CR^7R^8)—COR^3$ $R^1R^2C(CR^4R^5-CR^6=CR^7R^8)-COR^3$ wherein $R^1$ and $R^2$ are independently H, alkyl, aryl, carbocyclic, heterocyclic, or chemical moieties comprising one or more atoms of O, N, S, X, or P, wherein X is halogen;

$COR^3$ is an amide, an ester, or a carboxyl group; and $R^4$–$R^8$ are independently H, aryl, or alkyl;

wherein the step of converting comprises converting the allyl functionality —$(CR^4R^5-CR^6=CR^7R^8)$ of the monomers to a structurally distinct functionality such that the set of monomers having converted allyl functionalities form a combinatorial chemical library, said method further comprising the step of covalently linking at least two monomers to form oligomers, wherein the monomers are selected from the group consisting of the at least two different α-allyl carbonyl monomers and the monomer derivatives thereof wherein the covalent linking is by a carbon—carbon bond.

3. A method of making a combinatorial chemical library, comprising the step of:

converting in parallel a set of at least two different α-allyl carbonyl monomers to form monomer derivatives, the monomers having a structure $R^1R^2C(CR^4R^5-CR^6=CR^7R^8)-COR^3$ wherein $R^1$ and $R^2$ are independently H, alkyl, aryl, carbocyclic, heterocyclic, or chemical moieties comprising one or more atoms of O, N, S, X, or P, wherein X is halogen;

$COR^3$ is an amide, an ester, or a carboxyl group; and $R^4$–$R^8$ are independently H, aryl, or alkyl;

wherein the step of converting comprises converting the allyl functionality —$(CR^4R^5-CR^6=CR^7R^8)$ of the monomers to a structurally distinct functionality such that the set of monomers having converted allyl functionalities form a combinatorial chemical library, said method further comprising the step of covalently linking at least two monomers to form oligomers, wherein the monomers are selected from the group consisting of the at least two different α-allyl carbonyl monomers and the monomer derivatives thereof further comprising the step of:

glycosylating the oligomers to form glycosylated oligomers.

4. A method of making a combinatorial chemical library, comprising the step of:

converting in parallel a set of at least two different α-allyl carbonyl monomers to form monomer derivatives, the monomers having a structure $R^1R^2C(CR^4R^5-CR^6=CR^7R^8)-COR^3$ wherein $R^1$ and $R^2$ are independently H, alkyl, aryl, carbocyclic, heterocyclic, or chemical moieties comprising one or more atoms of O, N, S, X, or P, wherein X is halogen;

$COR^3$ is an amide, an ester, or a carboxyl group; and $R^4$–$R^8$ are independently H, aryl, or alkyl;

wherein the step of converting comprises converting the allyl functionality —$(CR^4R^5-CR^6=CR^7R^8)$ of the monomers to a structurally distinct functionality such that the set of monomers having converted allyl functionalities form a combinatorial chemical library, said method further comprising the step of covalently linking at least two monomers to form oligomers, wherein the monomers are selected from the group consisting of the at least two different α-allyl carbonyl monomers and the monomer derivatives thereof further comprising the step of:

cyclizing the oligomers by means of an intramolecular reaction to form cyclized oligomers.

5. A method of making a combinatorial chemical library, comprising the step of:

converting in parallel a set of at least two different α-allyl carbonyl monomers to form monomer derivatives, the monomers having a structure $R^1R^2C(CR^4R^5-CR^6=CR^7R^8)-COR^3$ wherein $R^1$ and $R^2$ are independently H, alkyl, aryl, carbocyclic, heterocyclic, or chemical moieties comprising one or more atoms of O, N, S, X, or P, wherein X is halogen;

$COR^3$ is an amide, an ester, or a carboxyl group; and $R^4$–$R^8$ are independently H, aryl, or alkyl;

wherein the step of converting comprises converting the allyl functionality —$(CR^4R^5-CR^6=CR^7R^8)$ of the monomers to a structurally distinct functionality such that the set of monomers having converted allyl functionalities form a combinatorial chemical library, said method further comprising the step of covalently linking at least two monomers to form oligomers, wherein the monomers are selected from the group consisting of the at least two different α-allyl carbonyl monomers and the monomer derivatives thereof further comprising the step of:

cyclizing the oligomers by means of an intermolecular reaction to form cyclized oligomers.

\* \* \* \* \*